(12) United States Patent
Kraft et al.

(10) Patent No.: US 7,468,125 B2
(45) Date of Patent: Dec. 23, 2008

(54) SYSTEM AND METHOD OF PROCESSING A CURRENT SAMPLE FOR CALCULATING A GLUCOSE CONCENTRATION

(75) Inventors: Ulrich Kraft, Hofheim (DE); James Christol, Cupertino, CA (US); Manfred Ebner, Obersursel (DE)

(73) Assignee: Lifescan, Inc., Milpitas, CA (US)

( * ) Notice: Subject to any disclaimer, the term of this patent is extended or adjusted under 35 U.S.C. 154(b) by 0 days.

(21) Appl. No.: 11/252,216

(22) Filed: Oct. 17, 2005

(65) Prior Publication Data

US 2007/0087397 A1 Apr. 19, 2007

(51) Int. Cl.
*G01N 27/327* (2006.01)

(52) U.S. Cl. .................................. 205/792; 205/775

(58) Field of Classification Search ..................
204/403.01–403.15, 406, 416–420; 205/777.5,
205/778, 792, 775
See application file for complete search history.

(56) References Cited

U.S. PATENT DOCUMENTS

| | | | |
|---|---|---|---|
| 5,366,609 | A | 11/1994 | White et al. |
| 5,708,247 | A | 1/1998 | McAleer et al. |
| 6,046,051 | A | 4/2000 | Jina |
| 6,233,471 | B1 | 5/2001 | Berner et al. |
| 6,241,862 | B1 | 6/2001 | McAleer et al. |
| 6,733,655 | B1 | 5/2004 | Davies et al. |
| 6,946,299 | B2 * | 9/2005 | Neel et al. .............. 436/95 |
| 2003/0109798 | A1 | 6/2003 | Kermani |
| 2003/0217918 | A1 | 11/2003 | Davies et al. |
| 2004/0064133 | A1 | 4/2004 | Miller et al. |
| 2005/0027463 | A1 | 2/2005 | Goode et al. |
| 2007/0084734 | A1 | 4/2007 | Roberts et al. |

FOREIGN PATENT DOCUMENTS

| | | |
|---|---|---|
| EP | 1067384 A | 1/2001 |
| EP | 1318399 A | 6/2003 |
| EP | 1541998 A | 6/2005 |
| JP | 07-107531 B2 * | 11/1995 |
| WO | WO01/67099 | 9/2001 |
| WO | WO01/73124 | 10/2001 |
| WO | WO 2005/054846 A | 6/2005 |

OTHER PUBLICATIONS

JPO English language machine translation of Daikin Ind ltd (JP 07-107531 B2) Nov. 15, 1995.*
European Search Report, Munich, Germany, 01 17 2007, re Application EP06255299.7.
U.S. Appl. No. 11/252,296, filed Oct. 17, 2005, Roberts et al.
Certificate of Translation for Daikin Ind. Ltd. (JP 07-107531 B2) Nov. 15, 1995.
Translation of Daikin Ind. Ltd. (JP 07-107531 B2) Nov. 15, 1995.

* cited by examiner

*Primary Examiner*—Alex Noguerola

(57) ABSTRACT

A system and method of processing a test current for an analyte measurement in a fluid using a test strip and a test meter are disclosed. The method comprises sampling the test current at a pre-determined sampling rate to acquire a plurality of A/D conversions. The method also comprises filtering out at least a highest magnitude A/D conversion and a lowest magnitude A/D conversion leaving a plurality of accepted A/D conversions. Further, the method comprises calculating an average or a summation of the plurality of accepted A/D conversions and converting the average or the summation into a glucose concentration.

11 Claims, 8 Drawing Sheets

US 7,468,125 B2

SYSTEM AND METHOD OF PROCESSING A CURRENT SAMPLE FOR CALCULATING A GLUCOSE CONCENTRATION

BACKGROUND

The invention generally relates to a system for managing health care and, in particular, to a system for filtering electrical signals generated by a voltage provided to a test strip for testing physiological fluid in a test meter.

Diabetes is a chronic disease that requires continued monitoring and controlling of health parameters such as blood glucose levels, medication, nutritional condition, and weight and exercise data. Also, patients with cardiovascular disease may require the monitoring of cholesterol levels. Because of the chronic nature of such diseases, health parameters must be measured on a continual periodic basis by the patients themselves outside a clinical setting.

Conventionally electronic meters are used to measure glucose from a test strip when a patient applies blood to it. The test strip may be designed to include two or more electrodes connectable with a meter and used to develop an electrical pathway through the sample. The meter is then able to determine the electrical characteristics of the sample and through known correlations may be able to deduce the concentration of a particular analyte in the sample.

Conventional methods for the measurement of blood glucose response current use an analog to digital (A/D) converter. The A/D converter samples the voltage, which is generated from an electronic circuit, connected to the test strip. The current generated in the strip is very low, only a few microamperes and the resolution of the signal should be as high as possible to achieve a high resolution blood glucose signal. Because of all kinds of noise from the environment, measuring a very small signal with a high resolution by nature leads to technical difficulties. Such noise sources may include signals from light switches, mobile phones, electrostatic discharge pulses, power supplies connected to mains, etc. These disturbances add to the signal and falsify the measurement result.

Conventionally, there are hardware and software solutions to solving the noise problem. One example of a hardware solution may be to integrate the signal by, for example, using an R-C (resistor-capacitor) combination circuit. Such a circuit may be used to smooth the signal and improve the signal to noise ratio. However, the application of such a circuit introduces delays and reduces bandwidth.

An example of a software solution is to sample the signal as often as possible and then calculate an average of all values sampled. The principle is similar to the hardware integration, however it "weights" every sample the same. Accordingly, a very short glitch, which may occur just when the sampling starts, is given too much weight thereby overshadowing other signal changes during the conversion period and those signal changes may be ignored. Nevertheless, such a software solution usually reduces the noise to an acceptable "quasi noise-free" value, especially when it has to eliminate "white noise" effects. This principle however is limited when there is not sufficient time to take enough A/D readings or the noise is not "white noise". As more readings are being averaged, the final result will be more accurate. However, taking too many readings takes a significant amount of time. Also for the software solution to calculate the average produces a phase shifting of the real signal versus the average result. For example, taking readings from a constant changing signal like the blood glucose transient over a period of, for example, 200 ms will give an average value that is available 100 ms delayed and also corresponds to the mean value over the last 200 ms.

In blood glucose monitoring, the software averaging algorithm, described above, alone may not be sufficient to filter noise and provide a preferred level of performance because a "glitch" or noise disturbance, which does not accurately represent the electrical characteristics of the sample, may be so large as to dominate the smaller measured values which are closely representative of the true electrical characteristics of the sample. Accordingly, there is a need for an alternative filtering method which is tailored to eliminate "glitches" or noise disturbances like those generated from light switches, electrostatic discharge, switching power supplies, and also from the meter electronics itself, which may have microcontrollers with external address and data bus devices with switching frequencies in the megahertz (MHz) range. Thus, there is a need for a filtering algorithm which analyzes those values before a noise disturbance, which may only take a few microseconds, and may cause only one or two A/D readings to be wrong (usually extremely high or low) and identifies these "wrong" or "extreme" readings and filters them out before the average is calculated over the remaining value. Such a system would have a significant advantage over conventional methods, because less A/D readings would be required to come to a "quasi noise-free" result and thus much less time would be needed to take a sufficient number of samples. Such a methodology would also have the effect of reducing the phase delay.

The techniques herein below extend to those embodiments which fall within the scope of the appended claims, regardless of whether they accomplish one or more of the above-mentioned needs.

SUMMARY

Figure 1:
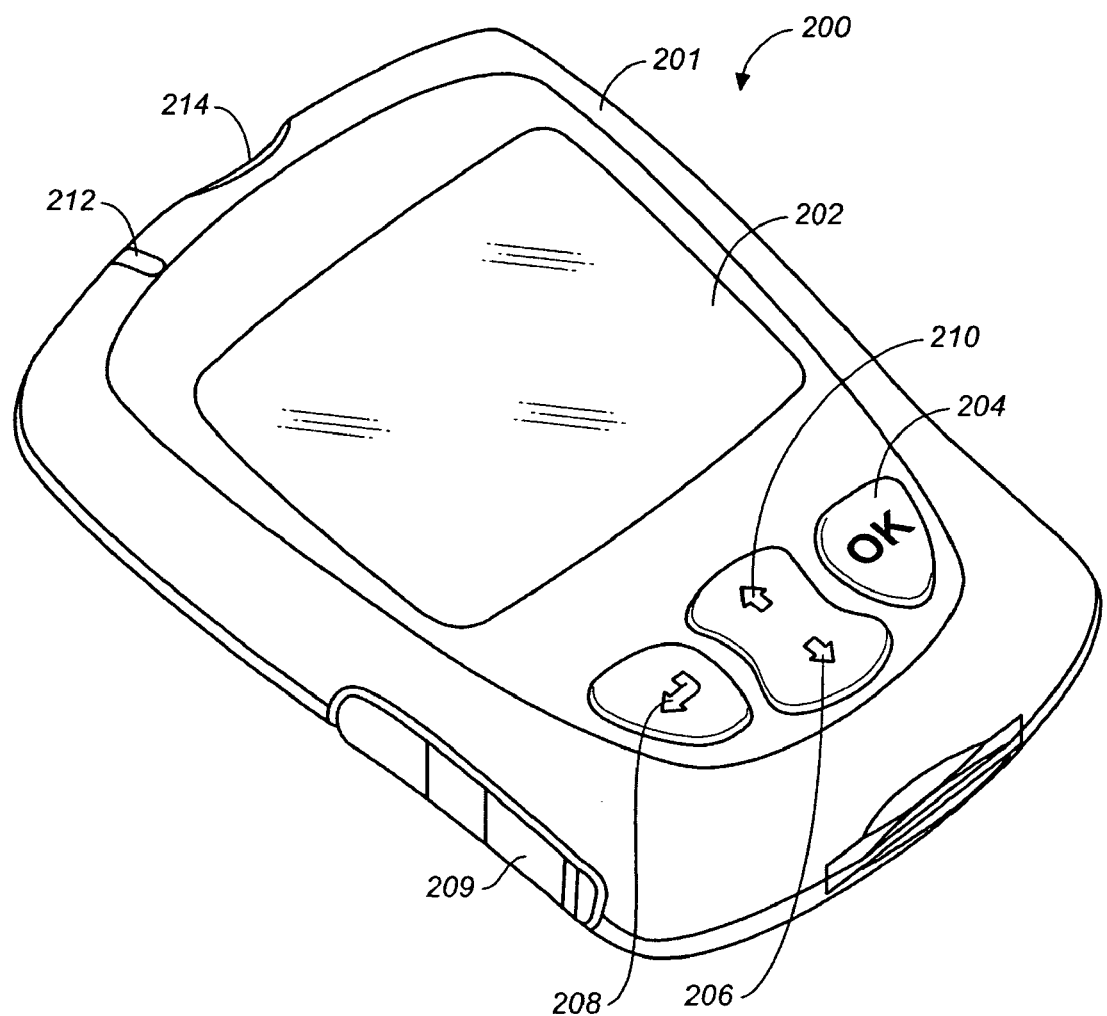
FIG. 1 is a perspective view of a test meter in accordance with an exemplary embodiment.

What is provided is a method of processing a test current for an analyte measurement in a fluid using a test strip and a test meter where the method comprises sampling the test current at a pre-determined sampling rate to acquire a plurality of A/D conversions. The method also comprises filtering out at least a highest magnitude A/D conversion and a lowest magnitude A/D conversion leaving a plurality of accepted A/D conversions. Further, the method comprises calculating an average or a summation of the plurality of accepted A/D conversions and converting the average or the summation into a glucose concentration.

What is also provided is a system for determining analyte concentration in a fluid. The system comprises a fluid receiving device for receiving a sample of fluid, the fluid receiving device having at least one pair of electrodes for applying a voltage thereto. The system also comprises a meter comprising a processor, a memory coupled to the processor, and an analog to digital converter coupled to the electrodes of the fluid receiving device, the analog to digital converter sampling an analog signal received from the fluid receiving device. Further, the system comprises a program stored in the memory and running on the processor, the program storing a plurality of analog to digital conversions, sorting the plurality of analog to digital conversions based on magnitude, discarding at least one of the highest magnitude analog to digital conversions, summing the remaining analog to digital conversions, and converting the sum to an analyte concentration measurement.

Further, what is provided is a method of determining analyte concentration in a physiological fluid. The method comprises receiving, by a test meter, a sample of physiological fluid. The method also comprises causing a current to run through the fluid sample. Further, the method comprises sampling the magnitude of the current a plurality of times to form a plurality of analog to digital (A/D) conversions. Further still, the method comprises discarding a subset of the plurality of A/D conversions, based on the magnitudes. Yet further still, the method comprises generating an analyte concentration based on the remaining A/D conversions.

Further still, what is provided is a particularly preferred method of processing a test current for an analyte measurement using a test strip and a test meter. The method comprises (a) sampling the test current at 40,000 Hz to acquire sixteen A/D conversions, (b) filtering out at least a four highest magnitude A/D conversions and a four lowest magnitude A/D conversions leaving 8 accepted A/D conversions and (c) calculating a current sample which includes a summation of said 8 accepted A/D conversions. The method also comprises (d) repeating steps (a) to (c) seven more times to calculate a total of 8 current samples, (e) summing together the 8 current samples to form a current reading and (f) repeating steps (a) to (e) four more times to calculate a total of 5 current readings. Further, the method comprises (f) summing together said 5 current readings to form a final current value; and (g) calculating a glucose concentration based on said final current value.

What is still further provided is a kit for determining analyte concentration in a fluid. The kit comprises at least one test strip for receiving a sample of fluid, the at least one test strip having at least one pair of electrodes for applying a voltage thereto. The kit also comprises a meter comprising a processor, a memory coupled to the processor, and an analog to digital converter coupled to the electrodes of the fluid receiving device, the analog to digital converter sampling an analog signal received from the fluid receiving device. Further, the kit comprises a program stored in the memory and running on the processor, the program storing a plurality of analog to digital conversions, sorting the plurality of analog to digital conversions based on magnitude, discarding at least one of the highest magnitude analog to digital conversions, summing the remaining analog to digital conversions, and converting the sum to an analyte concentration measurement.

Alternative exemplary embodiments relate to other features and combination of features as may be generally recited in the claims.

DETAILED DESCRIPTION

Generally a method for reducing the noise in a data acquisition process is disclosed. The method includes sampling an analog signal a plurality of times during a given time period. The plurality of analog to digital (A/D) conversions may be ranked based on their magnitude and instead of averaging all of the plurality of A/D conversions, specific samples are selected and discarded. An average of the remaining A/D conversions is then computed. In an exemplary embodiment, it may be desirable to discard at least a highest magnitude A/D conversion and at least a lowest magnitude A/D conversion. Alternatively, a number of highest conversions and a number of lowest conversions may be discarded. This filtering process has the effect of making the computed average more robust to extreme outliers that may be caused by environmental noise, such as, but not limited to electrostatic discharge. Accordingly, the resultant computed average is more accurate than a simple averaging methodology.

In accordance with an exemplary embodiment of the invention, a test meter and a disposable test strip may be used to perform a glucose test for measuring a concentration of glucose in a physiological fluid. An example of a test meter and a disposable test strip may be a commercially available OneTouch Ultra System kit from LifeScan, Inc. (Milpitas, Calif., U.S.A.). It should be noted that the system kit may include the disposable test strip and the test meter. The system test kit is not limited to these parts but may also include many others, such as but not limited to power supplies, batteries, documentation, etc.

FIG. 1 is a perspective view of an exemplary test meter 200 in accordance with an exemplary embodiment. Test meter 200 includes a housing 201, a display 202, an OK button 204, a down button 206, a back button 208, an up button 210, a light emitting diode (LED) 212, and a strip port connector (SPC) 214. Display 202 may be a liquid crystal display (LCD) to show both textual and graphical information to a user. A user interface (UI) may be software driven menu that is shown on display 202 that enables the user to operate test meter 200. A user can navigate through the UI using up button 210, down button 206, OK button 204, and back button 208. Test meter 200 is an example of one configuration of a test meter; there may be many others. Housing 201 may be formed from any of a variety of materials, including but not limited to polymeric materials, metals and metal alloys, etc. Display 202 may be any variety of display devices, including, but not limited to LCD displays, LED displays, OLED displays, and other types of displays which may be heretofore developed. Further, display 202 may be a series of lights and/or simple readouts as opposed to a single integrated display screen. LED 212 may be any other variety of indicators, including, but not limited to LED's, other types of light devices, sound devices, vibration devices, etc. Strip port connector 214 is used to accept and to electrically connect a test strip to test meter 200 however other configurations of interfacing devices may also be used. Buttons 204, 206, 208, and 210 may be any of a variety of buttons or other user input devices including, but not limited to touch sensitive devices. Further, buttons 204, 206, 208, and 210 may be replaced a user interface on display 202 or a speech recognition device built into test meter 200. Display 202 may also include a touch sensitive screen which overlays display 202 and allows a user to provide input to test meter 200 via the touch screen. In an exemplary embodiment, the touch sensitive screen may be used with a user's finger, a separate stylus or other touching device.

Figure 2:
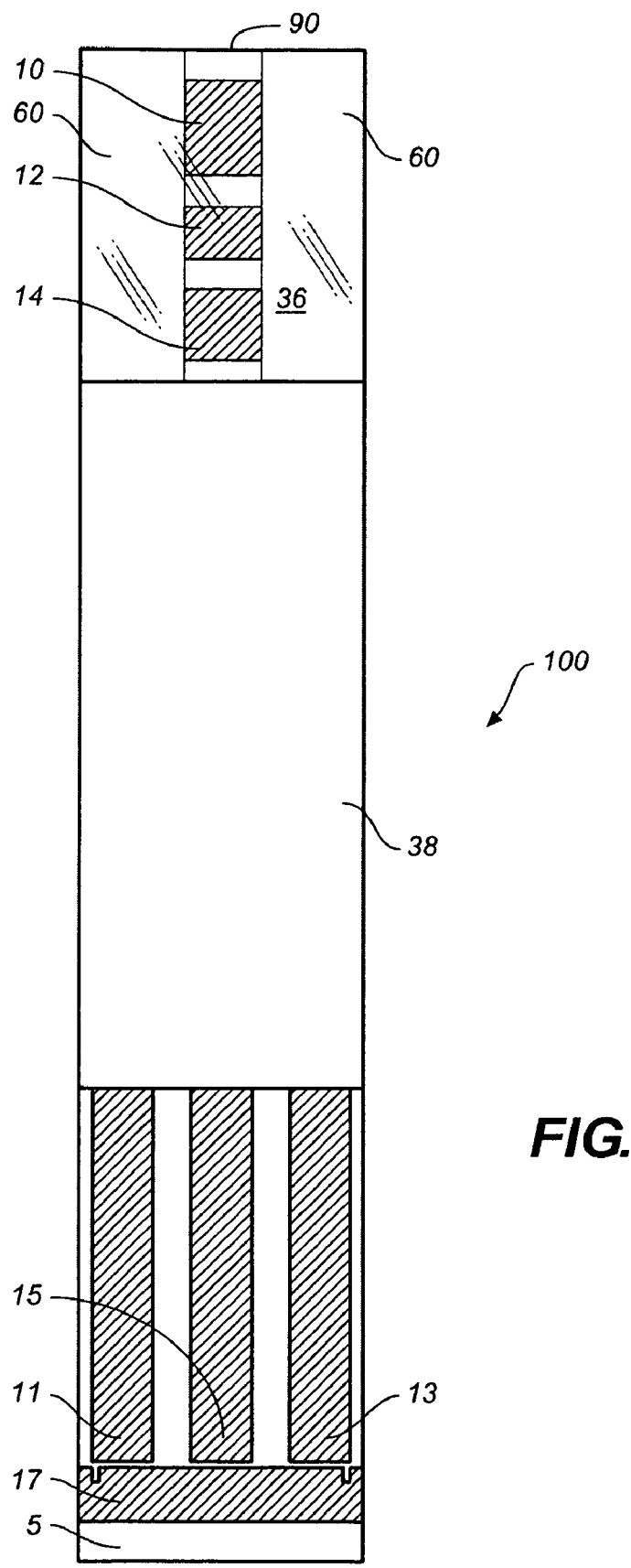
FIG. 2 is a plan view of a test strip suitable for use in the test meter as shown in FIG. 1.

A test strip 100 suitable for use in test meter 200 is shown in FIG. 2. Test strip 100 includes a conductive layer comprising electrically isolated portions that are conventionally printed onto a substrate 5. The conductive layer includes a first contact 13, a second contact 15, a reference contact 11, and a strip detection bar 17 which may be used to electrically connect to strip port connector 214. The conductive layer further includes a first working electrode 12, a second working electrode 14, and a reference electrode 10 which are electrically connected, respectively, to first contact 13, second contact 15, and reference contact 11. Contacts to the electrodes connect within the meter to apply a voltage across electrodes selectively under control of the meter. Test strip 100 further includes, but is not limited to, a clear hydrophilic film 36 which is bound by an adhesive 60 that forms a sample receiving chamber that allows blood to be dosed at an inlet 90. In an exemplary embodiment film 36 covers the entire end of the test strip thereby forming the visible sample chamber between the adhesion zones shown as 60 in FIG. 2. An opaque film 38 is also bound by adhesive 60 to show contrast for guiding user to dose blood at inlet 90. Substrate 5 may be formed of a variety of materials including, but not limited to polymeric materials or other insulating materials. In an exemplary embodiment, the material substrate 5 may be formed from a polyester material (such as, but not limited to Meline ST328), which is manufactured by DuPont Teijin Films. Substrate 5 may be supplied in a roll of material, which may be, for example, nominally 350 microns thick by 370 millimeters wide and approximately 660 meters in length. Conductive layers, such as layers 10, 11, 12, 13, 14, 15, and 17 may be formed from any of a variety of conductive materials such as, but not limited to metals and metal alloys which may be deposited on substrate 5 via any of a number of manufacturing processes. Opaque film 38 is used for the convenience of a user to provide contrast but may be substituted by any of a number of methods, such as printed textual indicators, to guide the user to dose blood at inlet 90. An example of test strip 100 is OneTouch Ultra which is available from LifeScan, Inc. (Milpitas, Calif., USA).

In accordance with an alternative exemplary embodiment, it may be desirable to provide a test strip which includes a working electrode and a reference electrode, as opposed to two working electrodes. Further, any of a variety of test strip configurations may be suitably substituted for test strip 100 without departing from the scope of the invention as long as test strip 100 is able to provide an electrical signal to test meter 200 when a physiological fluid sample is present.

A reagent layer (not shown) may be disposed on first working electrode 12, second working electrode 14, and reference electrode 10 within the sample chamber or cavity. Reagent layer may include chemicals such as a redox enzyme and mediator which selectively reacts with glucose. Examples of reagent formulations or inks suitable for use in making reagent layer 22 can be found in U.S. Pat. Nos. 5,708,247 and 6,046,051; Published International Applications WO01/67099 and WO01/73124, all of which are incorporated by reference herein. Further, any of a variety of other reagent layers and reagent chemicals may be used without departing from the scope of the invention. Alternatively, it may be possible to produce a test strip that does not utilize a reagent layer as disclosed in the references provided. Further still, it may not be required to have the reagent layer disposed on all of the electrodes 12, 14, and 10, Rather, the reagents may be disposed on any of the electrodes or other surfaces within the sampling region of the test strip.

Once test strip 100 is electrically connected to test meter 200 through strip port connector 214, a user may apply a physiological fluid to inlet 90. In accordance with alternative embodiments, test meter 200 may have different types of connectors as opposed to strip port connector 214. The scope of the invention may not be limited by the type of connector being used. Physiological fluid may be applied to test strip 100 in a variety of ways. The fluid sample may be taken from a droplet of blood on the skin surface, or from a receptacle. A physiological fluid sample may also be taken directly from the body by using a needle or microneedle. The physiological fluid causes the reagent layer to dissolve and enzymatically generate a proportional amount of reduced mediator which correlates to a glucose concentration. Test meter 200 may apply a test voltage of about +0.4 Volts, for example, between first working electrode 12 and reference electrode 10. The test meter can also apply a test voltage of about +0.4 Volts between second working electrode 14 and reference electrode 10. This will enable the reduced mediator to be proportionally measured as a test current, which in this case is an oxidation current measured at first working electrode 12 and at second working electrode 14. In accordance with alternative embodiments, the test voltage that is applied may be any of a variety of test voltages. The test voltages are not limited to the 0.4 Volts described above. Further, it may not be necessary to apply test voltages between both a first electrode and the reference electrode and a second electrode and the reference electrode. It may be desirable only to have a system which measures voltages between the first electrode and the reference electrode, thereby simplifying the system.

Figure 3:
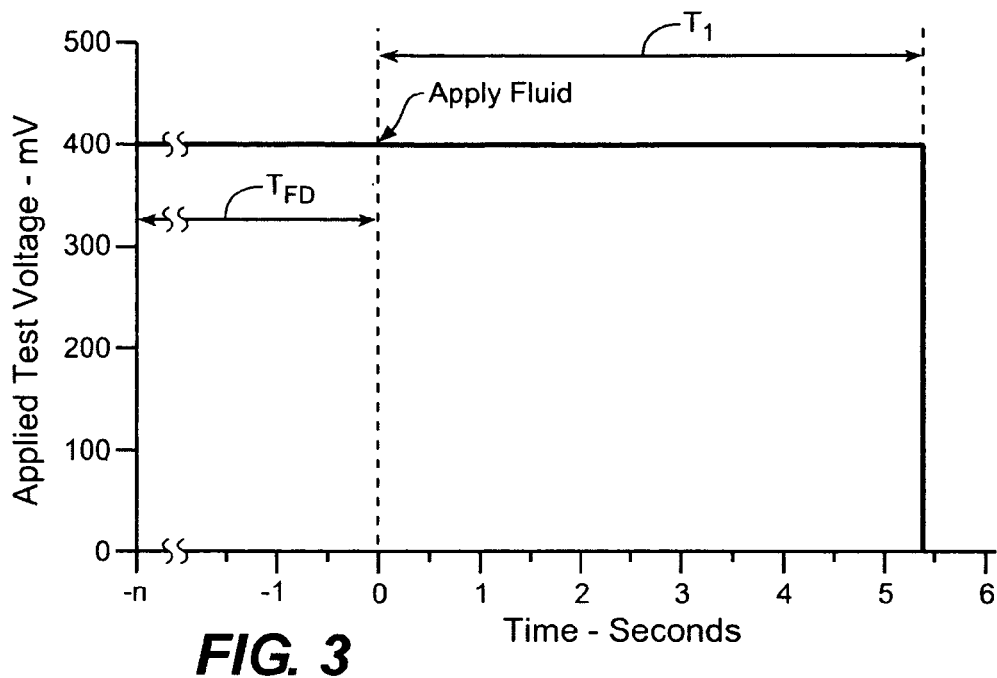
FIG. 3 is a chart showing a test voltage applied by the test meter to the test strip for a test time interval $T_1$.

FIG. 3 is an exemplary chart showing a test voltage applied by test meter 200 to test strip 100 for a test time interval $T_1$. Before the physiological fluid is applied, test meter 200 would be in a fluid detection mode in which the test voltage is +0.4V. The fluid detection mode is indicated in FIG. 3 as a fluid detection time interval $T_{FD}$ and as indicated is a time period before or less than a zero (0) reference time. In the fluid detection mode, test meter 200 determines when a fluid is applied to inlet 90 such that both first working electrode 12 and reference electrode 10 are wetted with a fluid. Note that first working electrode 12 and reference electrode 10 are effectively short-circuited when the physiological fluid contiguously covers first working electrode 12 and reference electrode 10. Once test meter 200 recognizes that the physiological fluid has been applied because of a sufficient increase in the measured test current between electrodes 10 and 12, test meter 200 assigns a zero second marker and starts the test time interval $T_1$. In accordance with other exemplary embodiments, other methods of determining the presence of a physiological fluid on the test strip may be used. For example, other methods of detecting the presence of a fluid on the test strip may be used. Further, it may be possible to manually indicate to the test meter when to start the test time interval. Accordingly, although the described methodology for detecting an applied fluid and for determining when to start the test time interval, may be effective, other methods either known or later developed may be used without departing from the scope of the invention.

In an exemplary embodiment of this invention, test time interval $T_1$ may be about 5.4 seconds. During the first time interval, the sample current is measured and the data collected to determine the glucose concentration in the sample. Upon the completion of the test time interval $T_1$, the test voltage is removed. While an effective test time has been shown to be 5.4 seconds, any of a variety of test times may be used.

Figure 4:
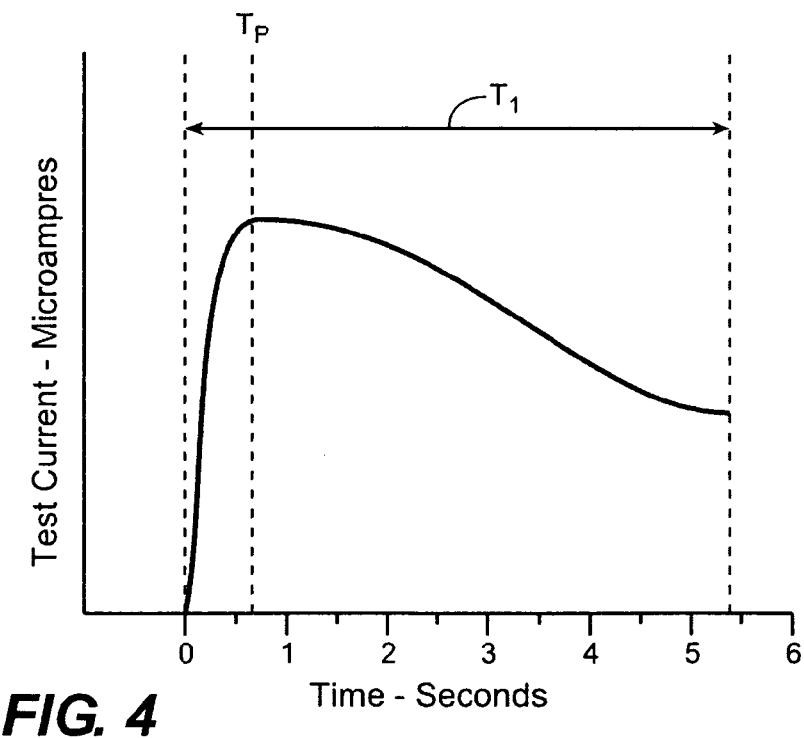
FIG. 4 is a chart showing a test current generated by the test strip for test time interval $T_1$.

In accordance with an exemplary embodiment, test strip 100 will carry a test current when the test voltage is sufficiently positive with respect to a redox potential of the mediator. Note that a redox potential describes a mediator's intrinsic affinity to accept or donate electrons when sufficiently close to an electrode having a nominal potential. FIG. 4 is an exemplary chart showing the test current detected flowing through the sample on test strip 100 for test time interval $T_1$. The meter coupled to test strip 100 is configured to measure the current in the circuit formed by the two electrodes and the sample in the sample area. In general, the test current rapidly increases when test strip 100 is initially wetted with the physiological fluid causing a peak to be formed which is followed by a gradual decrease in the test current. While FIG. 4 represents a typical test, other response curves may be observed, especially but not only, in the testing for other analytes besides glucose as well as the presence of other noise disturbances.

It should be noted that the test current in FIG. 4 is an analog signal that may be converted to a digital signal for processing the test current into a glucose concentration. In an exemplary embodiment of this invention, test meter 200 may include a Texas Instrument mixed signal processor (e.g. TI MSP 430) having a twelve bit A/D converter for converting the analog test current into a digital test current. Other A/D converting circuits may similarly be used, including those with more or less bits providing differing accuracy and resolution, and those made or provided by different manufacturers. In an exemplary embodiment of this invention, the test current must be measured with a sufficiently high signal to noise (S/N) ratio such that a variation of the acquired digital signal may be less than about 5% CV (coefficient of variation, % CV={one standard deviation/average}×100), preferably less than about 3% CV, more preferably less than about 1% CV, and even more preferably less than about 0.1% CV. Other S/N ratios may be used, not limited to those explicitly provided. Further, although characterized by % CV, other characterizations of S/N ratio may also be used without departing from the scope of the invention. In an exemplary embodiment, a method will be described that reduces the noise in sampling the test current using an A/D converter.

Figure 5:
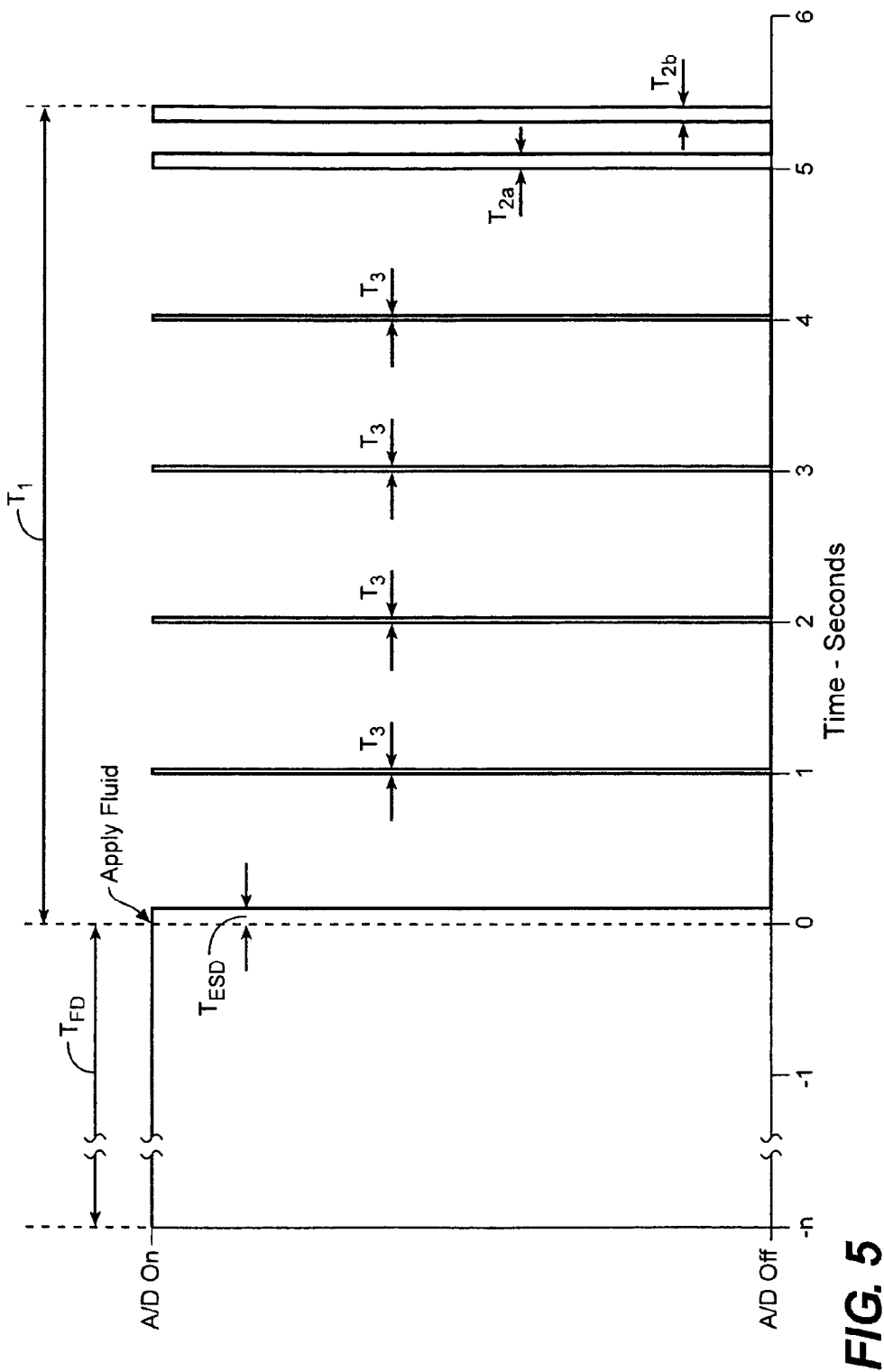
FIG. 5 is a simplified chart showing a plurality of time intervals for sampling the test current for a glucose test in accordance with an exemplary embodiment.
Figure 6:
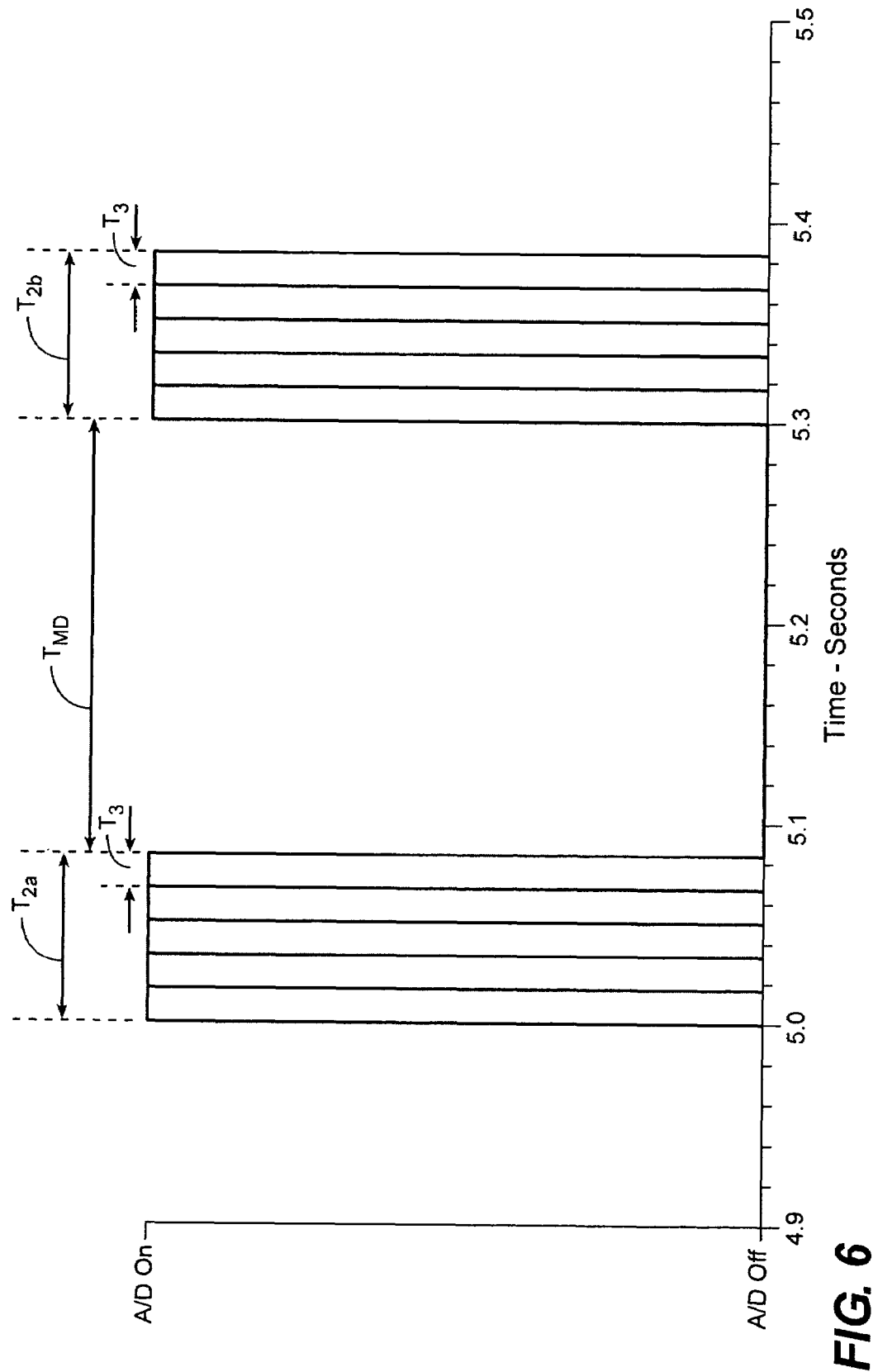
FIG. 6 is an expanded simplified view of a final current value time interval for first working electrode $T_{2a}$ and a final current value time interval for second working electrode $T_{2b}$, where each final current value time interval includes five consecutive current reading time intervals $T_3$.
Figure 7:
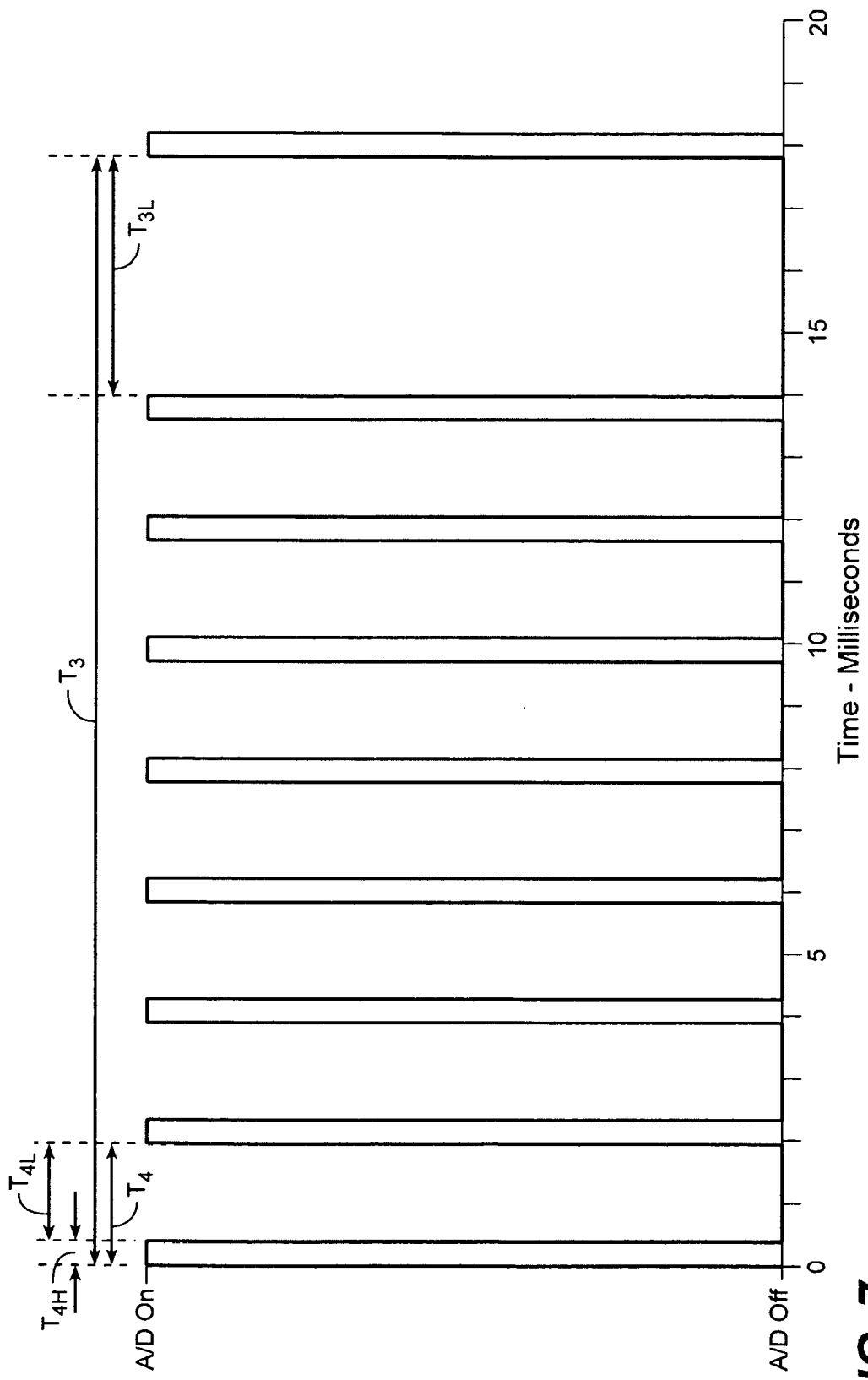
FIG. 7 is an expanded simplified view of a current reading time interval $T_3$ which includes eight consecutive current sample time intervals $T_4$.
Figure 8:
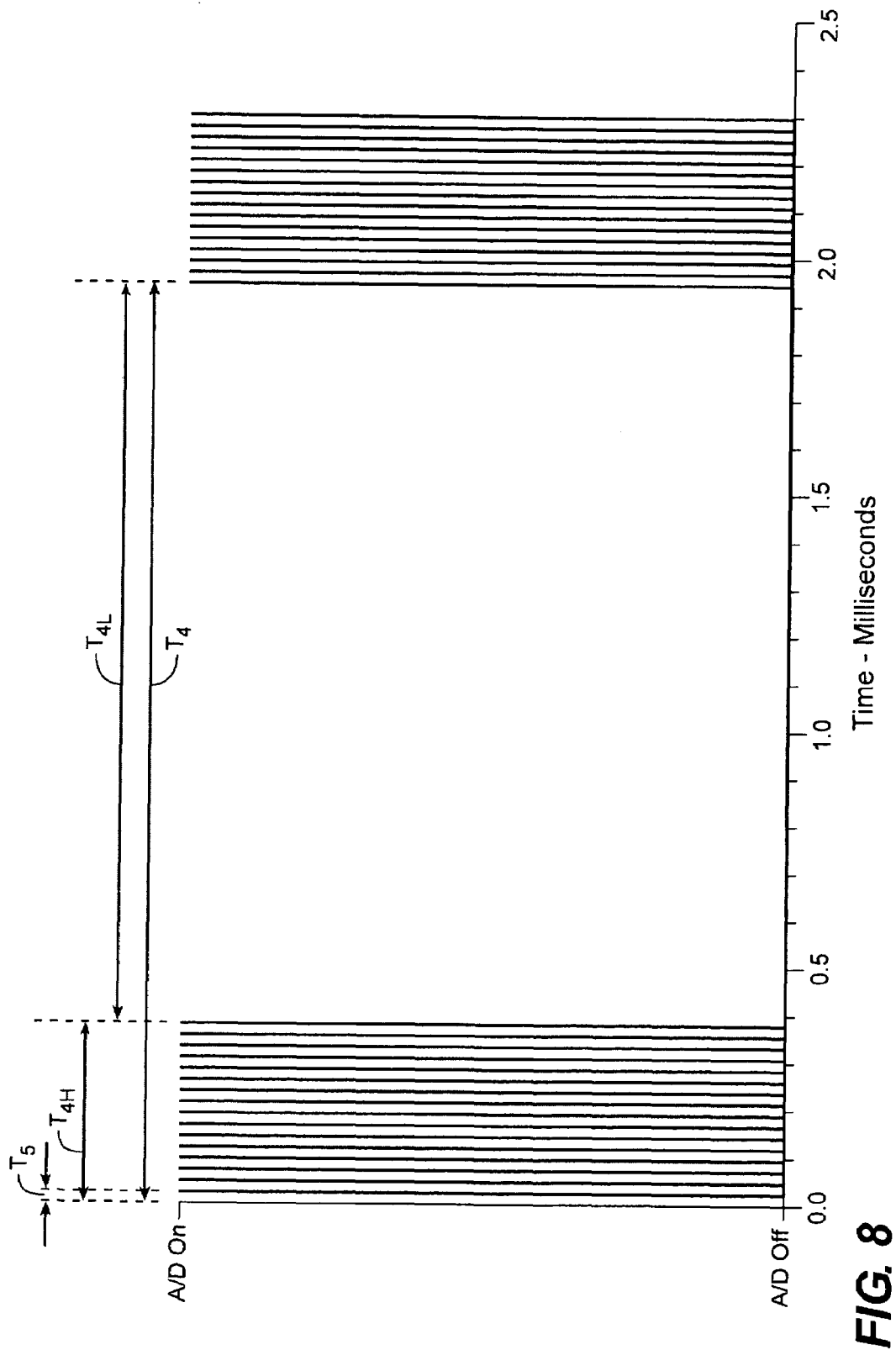
FIG. 8 is an expanded view of a current sample time interval $T_4$ which includes 16 consecutive A/D conversion time intervals $T_5$.

FIG. 5 is an exemplary simplified chart showing a plurality of time intervals for sampling the test current for a glucose test in accordance with an exemplary embodiment. Test time interval $T_1$ may include an aggregate of shorter time intervals which are a current reading time interval $T_3$, an electrostatic discharge (ESD) check time interval $T_{ESD}$, a final current value time interval for first working electrode $T_{2a}$, and a final current value time interval for second working electrode $T_{2b}$. Alternatively, other combinations of time intervals may be used having differing relative lengths. Further, some time intervals may be omitted in alternative embodiments. In FIG. 5, the A/D may toggle relatively quickly between the On and Off state during a given time interval, typically on the order of milliseconds or, in alternative embodiments on the order of microseconds. However, in FIG. 5 the shorter time intervals are shown as being continuously On because the time scale of the chart cannot clearly show a relatively high toggle rate. Note that FIGS. 6 to 8 show expanded portions of $T_{2a}$, $T_{2b}$, and $T_3$ to illustrate more accurately if a particular time interval has a higher switching frequency of the A/D conversions between the On and Off state. It should be noted that the sampling frequencies are not limited to those depicted, rather any frequencies may be used that yield desired performance.

FIG. 6 is an expanded simplified view of final current value time interval for first working electrode $T_{2a}$ and final current value time interval for second working electrode $T_{2b}$. In an exemplary embodiment of this invention, final current value time interval for first working electrode $T_{2a}$ starts at about 5 seconds and has a duration of about 80 milliseconds. Similarly, final current value time interval for second working electrode $T_{2b}$ starts at about 5.3 seconds and has a duration of about 80 milliseconds. There may be a measurement delay time interval $T_{MD}$ of about 300 milliseconds between final current value time interval for first working electrode $T_{2a}$ and final current value time interval for second working electrode $T_{2b}$. The invention is not limited to those specific time periods provided above, rather any time periods may be used that yield desired performance.

In an exemplary embodiment, final current value time interval for first working electrode $T_{2a}$ may include, for example, five consecutive current reading time intervals $T_3$. Similarly, final current value time interval for the second working electrode $T_{2b}$ may include, for example, five current reading time intervals $T_3$. Current reading time interval $T_3$ may be, for example, about 18 milliseconds as shown in FIGS. 6 and 7. The invention is not limited to the numbers of current reading time intervals disclosed nor to the reading time interval disclosed.

FIG. 7 is an expanded simplified view of a current reading time interval $T_3$ which includes eight consecutive current sample time intervals $T_4$. There is a LOW period reading time interval $T_{3L}$ that represents a period of time in which the A/D is Off after acquiring the A/D conversions, for example, for eight current sample time intervals $T_4$. During LOW period reading time interval $T_{3L}$, the microprocessor has a free time period to perform data calculations such as, for example, a summation or average of the A/D conversions acquired during current reading time interval $T_3$. At the end of LOW period reading time interval $T_{3L}$, the microprocessor may initiate another current reading time interval $T_3$. Again, the invention is not limited to the time intervals shown and disclosed nor to the number of A/D conversions shown and disclosed.

Current sample time interval $T_4$ may be, for example, about 2 milliseconds as shown in FIGS. 7 and 8. Current sample time interval $T_4$ includes a HIGH period sample time interval $T_{4H}$ and a LOW period sample time interval $T_{4L}$. HIGH period sample time interval $T_{4H}$ may be a period of time in which the A/D is On for acquiring A/D conversions. LOW period sample time interval $T_{4L}$ may be a period of time in which the A/D is Off after acquiring the required A/D conversions during HIGH period sample time interval $T_{4H}$. HIGH period sample time interval $T_{4H}$ may be, for example, about 0.4 milliseconds and LOW period sample time interval $T_{4L}$ may be, for example, about 1.6 milliseconds as shown in FIGS. 7 and 8. During LOW period sample time interval $T_{4L}$, the microprocessor has a free time period to perform data calculations on the acquired A/D conversions acquired during HIGH period sample time interval $T_{4H}$ such as, for example, ranking, filtering, summations, averaging and/or combinations thereof of the A/D conversions or other needed calculations and data manipulations. At the end of LOW period sample time interval $T_{4L}$, the microprocessor may initiate another current sample time interval $T_4$. The sample time interval magnitudes shown and described are not limited. Any time intervals maybe used which would provide desired performance.

FIG. 8 is an expanded view of an exemplary current sample time interval $T_4$ which includes 16 consecutive A/D conversion time intervals $T_5$. The test current may be sampled at a pre-determined sampling rate during HIGH period sample time interval $T_{4H}$. The pre-determined sampling rate may be, for example in an exemplary embodiment, about 40 Kilohertz as shown in FIG. 8. A single A/D conversion may be acquired during A/D conversion time interval $T_5$ which in this case may be about, for example, 25 microseconds as shown in FIG. 8. An A/D conversion would be a digital number having a magnitude which is proportional to the test current at the point in time in which the A/D conversion was taken. A/D conversions may also be referred to as a glucose signal because the magnitude of the A/D conversion in this case is proportional to the glucose concentration. Thus in accordance with an exemplary embodiment, 16 A/D conversions may be acquired during current sample time interval $T_4$ and stored in a memory portion of test meter 200. A current sample may then be calculated using either an average or summation of the 16 A/D conversions acquired during current sample time interval $T_4$. In an embodiment of this invention for reducing noise, a current sample may be calculated using either an average or summation of a subset of the 16 A/D conversions acquired during current sample time interval $T_4$. In an exemplary embodiment, a method will be described that shows how to select a subset of the 16 A/D conversions for reducing the noise when measuring a "current reading." In accordance with alternative embodiments, it may be desirable to discard one or more of the 16 samples acquired for the noise filtering process. Further, it may also be desirable to use more or less than 16 A/D conversions to meet desired performance goals and statistically significant objectives.

Figure 9:
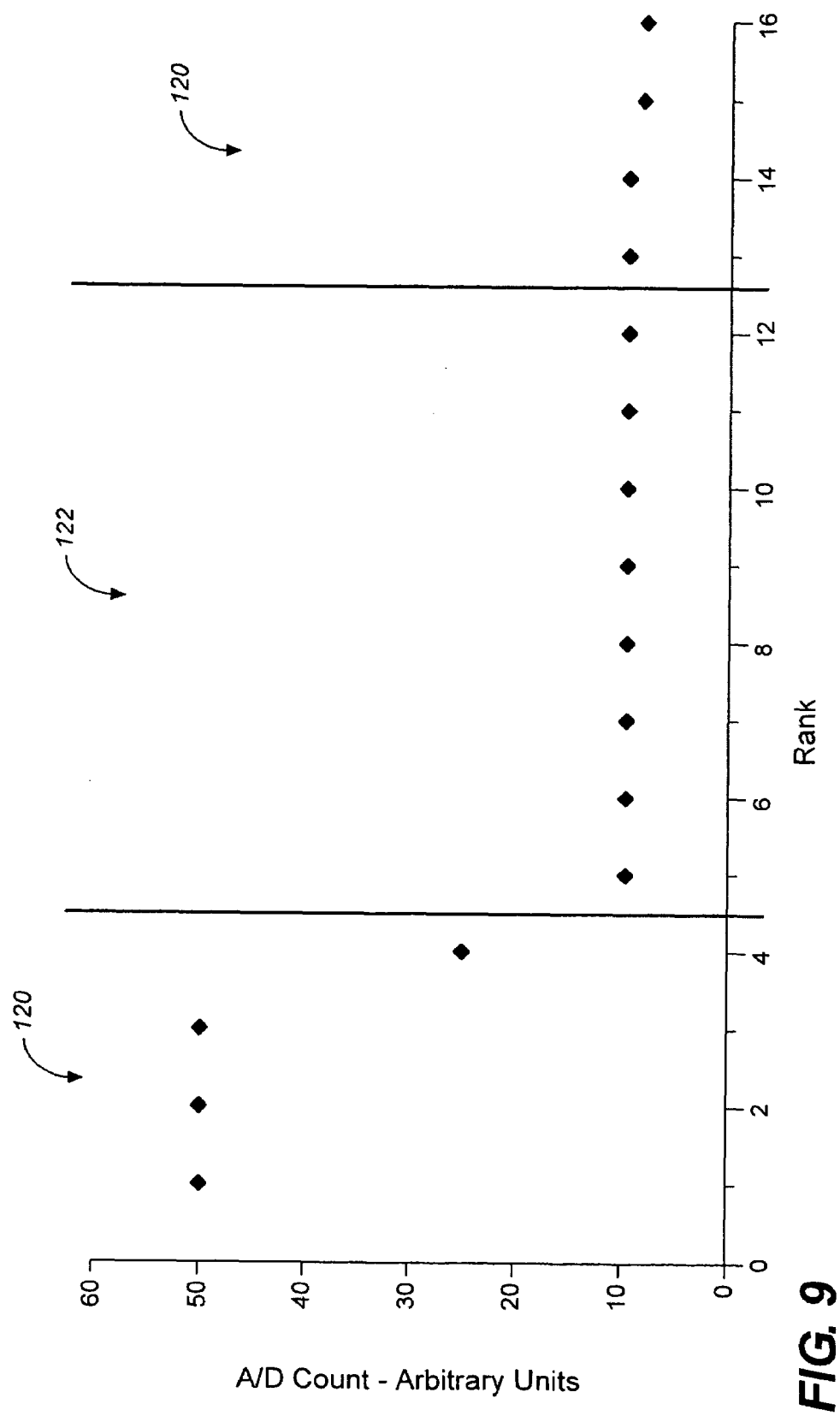
FIG. 9 is a chart showing a non-parametric method of filtering 16 A/D conversions which were acquired during current sample time interval $T_4$ according to an exemplary embodiment.

In general, an exemplary method for reducing noise is to average a plurality of A/D conversions. However, averaging will effectively reduce noise when it follows a Gaussian distribution. For situations in which the noise does not follow a Gaussian distribution, non-parametric methods may be used to help reduce noise. An example of noise which does not follow a Gaussian distribution may be an electrostatic discharge event, signals from light switches, and mobile phones. In an exemplary embodiment, sixteen A/D conversions collected during a current sample time interval $T_4$ may be ranked based on their magnitude as shown in FIG. 9. Instead of simply averaging all sixteen A/D conversions, at least a highest magnitude A/D conversion and a lowest magnitude A/D conversion may be filtered leaving a plurality of accepted A/D conversions. In an exemplary embodiment, only the accepted A/D conversions would be averaged or summed together. Because the highest and lowest A/D conversions are discarded, this makes the average more robust to extreme outliers which may be caused by short term events such as electrostatic discharge. In general, extreme outliers tend to significantly perturb averages making Gaussian statistics ineffectual. Although 16 samples provide good performance in the system described, the invention is not limited to 16 samples. Depending on the desired performance and the application of the filter other numbers of samples may be found to be more or less effective.

In another exemplary embodiment, a four highest A/D conversions and a four lowest A/D conversions may be filtered leaving eight accepted A/D conversions as shown in FIG. 9. FIG. 9 depicts high and low filtered zones 120 and an accepted zone 122. Filtered zone 122 shows the eight remaining samples that will be used for averaging while zones 120 show the eight samples which will be discarded. The microprocessor of test meter 200 may calculate a current sample by averaging or summing together the 8 accepted A/D conversions acquired during current sample time interval $T_4$. Next, a current reading may be calculated by averaging or summing together 8 current samples (of time $T_4$, which in this case is a total of 64 A/D conversions) all acquired within current reading time interval $T_3$. After calculating the current reading, a final current value may be calculated by averaging or summing together 5 current readings (which in this case is a total of 320 A/D conversions) all acquired within final current value time interval for first working electrode $T_{2a}$ or final current value time interval for second working electrode $T_{2b}$. In an exemplary embodiment, methods will be described for using current readings and final current values for determining whether a test strip has been dosed with a physiological fluid, calculating a glucose concentration, performing error trapping procedures, and preventing a glucose test from initiating when ESD is injected into the test meter. Further, in accordance with other exemplary embodiments, different numbers of A/D conversions, samples, and reading may be used. Also, it may be possible to use a single working electrode or more than two working electrodes without departing from the scope of the invention.

In an exemplary embodiment, a final current value for first working electrode and a final current value for second working electrode may be summed together to give a grand summation. A glucose algorithm may include the steps of subtracting a background value (which is representative of general background noise and therefore represents a bias) from the grand summation followed by a division of a calibration slope (which calibrates the device to known glucose concentration/current curves or data) to generate a glucose concentration which can be outputted onto display 202. By using a method of an exemplary embodiment of filtering the four highest and four lowest A/D conversion in the calculation of a current sample, a glucose concentration can be calculated that is sufficiently accurate and precise. Although this is one method of determining the glucose concentration, other methods may be applied to provide the final calculation, including look-up tables and other mathematical formulations. Similarly other processes may be used for different types of analytes.

The test current measured for a test strip 100 may have a characteristic shape as shown in FIG. 2 that is usually present when testing with a physiological fluid. If the characteristic shape is not present, then this is usually indicative of a system defect or a user error. More particularly, FIG. 2 shows an example of a test current that forms a maximum peak value followed by a gradual decay. In an exemplary embodiment, an error trapping method may include verifying that the test current does not increase after the maximum peak time $T_p$. The error trapping method may include determining a maximum peak value time and measuring a current reading at one second intervals as shown in FIG. 5 after applying fluid to test strip 100. The error trapping method may determine that there is no defect if a current reading minus an immediately previous current reading is less than an error threshold such as for example, about 100 nanoampres. This error trapping method may be performed on all current readings measured at one second intervals so long as the immediately previous current reading was measured after the maximum peak value time. As an example, if $I_{CRk} - I_{CRk-1} \leq 100$ nanoampres, then there is no error due to a non-characteristic increase in current with time where $I_{CRk}$ is the current reading at k seconds and $I_{CRk-1}$ is the current reading at k−1 seconds. However, if $I_{CRk} - I_{CRk-} > 100$ nanoampres, then test meter 200 should output an error message on display 202 and not output a glucose concentration. Likewise, other data integrity or error trapping methods may be applied without departing from the scope of the invention.

In another exemplary embodiment, a simplified error trapping method may be used. In this simplified embodiment, only two current readings are used at four seconds and at five seconds. The current reading at four seconds may be subtracted from the current reading at five seconds. If $I_{CR5} - I_{CR4} \leq 100$ nanoampres, then there is no error due to the non-characteristic increase in current with time, where $I_{CR5}$ is the current reading at 5 seconds and $I_{CR4}$ is the current reading at 4 seconds. However, if $I_{CR5-ICR4}>100$ nanoampres, then test meter 200 should output an error message on display 202 and not output a glucose concentration. In this simplified exemplary embodiment, current readings are not used at one, two, and three seconds so as to simplify the error trapping algorithm. Additionally, maximum peak time $T_p$ is also not calculated in this embodiment.

An exemplary embodiment is particularly useful for distinguishing current signals caused by extraneous events from a current signal that provides desired information such as one indicative of a measurement error. Extraneous signals can come from a variety of sources, events, or conditions and typically occur during the normal use of a test meter such as the test meter 200. Exemplary extraneous events include electrostatic discharge and electromagnetic emission such as radio-frequency or microwave frequency emission, for example. Use of an electronic device such as a phone, microwave oven, radio, or other household appliance can potentially cause an extraneous signal. Also, common events such as switching of light switches, switching of thermostats, and other activities were an electronic relay or the like turns on an off can cause extraneous signals.

In accordance with an exemplary embodiment, a particular extraneous signal can be characterized in some way and used to distinguish the extraneous signal from a desired signal. Characterization in this way preferably relates to the magnitude, duration, and timing (independently or in combination) of an extraneous signal. Generally, a characteristic behavior of an extraneous signal or event can be used to identify the signal as extraneous. This behavior may be a specific value or may relate to a trend or changing condition over time, for example.

One type of extraneous signal is related to electrostatic discharge. Under certain conditions, such as where low relative humidity exists, a user can carry a significant amount of electrostatic charge. Thus, such a user may potentially inject electrostatic energy into the test meter, when touching a test strip connected to a test meter. This unexpected energy can cause the meter to measure a sufficiently large current that can cause the meter to initiate and perform a glucose test on a dry test strip. Because there is no glucose in the test strip, the meter should output an error message because the measured test current will be too low. Typically, a user will be instructed to discard the test strip when the meter generates an error message. This is highly undesirable where ESD falsely triggers a glucose test because the dry test strip is actually not defective and thus would be thrown away unnecessarily.

In another exemplary embodiment, a method for preventing ESD from triggering a glucose test will be described. This material is also described in U.S. application Ser. No. 11/252, 296, entitled METHODS FOR MEASURING PHYSIOLOGICAL FLUIDS, filed on the same day herewith and herein incorporated by reference in its entirety. In use, test meter 200 preferably starts a fluid detection mode once test strip 100 is inserted into strip port connector 214. During the fluid detection mode, test meter 200 preferably applies a test potential of between at least the first working electrode 12 and the reference electrode 10. The test voltage used generally depends of the particular test meter and test strip used and a suitable test voltage for the illustrated meter 200 is about 400 millivolts. The fluid detection mode time interval TFD includes the time before physiological fluid is applied to inlet 90 and is represented as the time interval that is less than zero as illustrated in FIG. 5. During fluid detection mode time interval TFD, test meter 200 will preferably continuously measure a current reading at a predetermined frequency until a single current reading is found to exceed a threshold value. As an example a measurement frequency ranging from about once every 20 milliseconds to about once every 100 milliseconds can be used. A threshold value that can be used for testing blood is about 150 nanoamperes. When test strip 100 is initially dry, test meter 200 will measure a zero test current value or a small test current value which is below the threshold. Once fluid is applied, the test meter will measure an increase in a current reading due to a decrease in resistance between the first working electrode 12 and reference electrode 10. This current increase will cause the meter to start test time interval T1 as shown in FIG. 5.

As a precautionary measure, test meter 200 preferably enters an ESD check mode in accordance with an exemplary embodiment once test meter 200 measures at least one current reading greater than the threshold as shown in FIG. 5. In the ESD check mode, test meter 200 preferably continues to apply a potential for an ESD check time interval TESD. During the ESD check mode, test meter 200 preferably continuously measures a current reading on a predetermined schedule. For example, a measurement once every 20 milliseconds can be used. If any of the current readings measured during ESD check time interval TESD are less than the threshold, then test meter 200 preferably returns back to the fluid detection mode. If all of the current readings measured during ESD check time interval TESD are greater than the threshold, then test meter 200 will continue the glucose test.

For the case in which a physiological fluid such as blood is applied to test strip 100, a test current will be seen to increase for about 1 second as shown in FIG. 4. Therefore, test meter 200 will measure an increase in a current reading of greater than about 150 nanoampres due to a decrease in resistance between the first working 12 electrode and reference electrode 10. This will preferably cause the meter to go from the fluid detection mode to the ESD check mode. Typically, the test current will stay greater than 150 nanoampres for the ESD check time interval TESD allowing the glucose test to proceed through the test time interval T1.

For the case in which a sufficiently large ESD is injected into test meter 200, a current reading may be measured that is greater than the threshold causing the meter to go from the fluid detection mode to the ESD check mode. Typically, a test current generated by ESD dissipates quickly producing a transient spike that typically decays within about a 100 millisecond range. This contrasts with the increase in the test current caused by a test fluid such as blood where the test current continues to increase beyond a threshold of 150 nanoampres for a known time for the particular fluid (about 1 second for blood). Thus, when ESD is injected into test meter 200, at least one of the current readings measured during ESD check time interval TESD should be less than the threshold. When the ESD check time interval TESD expires, the flag is checked and if set, operation reverts back to looking for sample again. If the flag is not set, fluid measurement preferably continues as described below.

Preferably, where a fluid such as blood is being measured, ESD check time interval TESD ranges from about 100 milliseconds to about 1 second, and preferably be about 200 milliseconds. The low end of ESD check time interval TESD is based on a typical dissipation time of ESD, which is about 100 milliseconds but may be based on a typical characteristic such as a dissipation time for any desired extraneous event. The high end of ESD check time interval TESD is preferably based on the amount of available time before test meter 200 needs to notify a user that the test is in progress. For example, when a test meter performs a glucose test, a countdown of test time interval T1 is typically outputted onto a display of the test meter 200 in integer values. After one second has elapsed on the display, the user will believe that the glucose test is in progress. Therefore, when a sufficiently large amount of ESD is injected into test meter 200, it needs to determine that it must go back to the fluid detect mode before the user has any indication that the test is in progress such as when the display shows that one second of the glucose test has elapsed.

A meter, such as the meter 200, can be programmed so that after a first trigger reading (a measurement above a predetermined threshold) the meter continues to monitor the current for some predetermined period of time. The threshold may be a current level indicative of the presence of a sample for example. If during the monitoring period the current falls below the trigger threshold, the meter will set a flag. When the monitoring time expires, the flag will be checked and if set, operation will revert back to looking for sample again. If the current remains above the threshold for the whole of this period then the test sample current readings can be processed as normal. Monitoring the current for the whole of the ESD check period instead of reverting back once ESD is first detected can ensure that any ringing of the ESD pulse has time to decay before the meter attempts another reading.

It should be noted that the time intervals and current magnitudes disclosed relating to the ESD check are not limited to those disclosed. Other values may be used without departing from the scope of the invention.

While the detailed drawings, specific examples, and particular formulations given described exemplary embodiments, they serve the purpose of illustration only. It should be understood that various alternatives to the embodiments of the invention described maybe employed in practicing the invention. It is intended that the following claims define the scope of the invention and that structures within the scope of these claims and their equivalents be covered thereby. The hardware and software configurations shown and described may differ depending on the chosen performance characteristics and physical characteristics of the computing and analysis devices. For example, the type of computing device, communications bus, or processor used may differ. The systems shown and described are not limited to the precise details and conditions disclosed. Method steps provided may not be limited to the order in which they are listed but may be ordered any way as to carry out the inventive process without departing from the scope of the invention. Furthermore, other substitutions, modifications, changes and omissions may be made in the design, operating conditions and arrangements of the exemplary embodiments without departing from the scope of the invention as expressed in the appended claims

What is claimed is:

1. A method of determining analyte concentration in a physiological fluid, comprising:
   receiving, by a test meter, a sample of physiological fluid;
   causing a current to run through the fluid sample;
   sampling the magnitude of the current a plurality of times to form a plurality of analog to digital (A/D) conversions;
   discarding a subset of the plurality of A/D conversion, based on the magnitudes;
   generating an analyte concentration based on the remaining A/D conversions;
   determining a maximum current peak time;
   determining a change in current after the maximum current peak time during a time interval; and
   selectively indicating an error based on the change in current.

2. A method of determining analyte concentration in a physiological fluid, comprising:
   receiving, by a test meter, a sample of physiological fluid;
   causing a current to run through the fluid sample;
   sampling the magnitude of the current a plurality of times to form a plurality of analog to digital (A/D) conversions;
   discarding a subset of the plurality of A/D conversion, based on the magnitudes; and
   generating an analyte concentration based on the remaining A/D conversions, wherein a first subset of the plurality of A/D conversions is sampled from a first pair of electrodes and a second subset of the plurality of A/D conversions is sampled from a second pair of electrodes.

3. A method to determine analyte concentration in a fluid sample in contact with two electrodes, the method comprising:
   applying a voltage to the electrodes;
   sampling the magnitude of current generated in the fluid sample to provide a plurality of analog-to-digital conversions;
   discarding a subset of the plurality of analog-to-digatal conversions;
   generating an analyte concentration based on remaining analog-to digital conversions;
   determining a maximum current peak time;
   determining a change in current after the maximum current peak time during a time interval; and
   selectively indicating an error based on the change in current.

4. The method of claim 3, wherein the step of generating an analyte concentration based on the remaining A/D conversions comprises:
   repeating the steps of sampling, discarding and generating more than once to calculate a total more than one current samples; and
   summing together said more than one current samples to form a current reading.

5. The method of claim 4, further comprising:
   repeating the steps of repeating and summing at least one more times to calculate a total at least two current readings;
   summing together said at least two current readings to form a final current value; and
   calculating a glucose concentration based on said final current value.

6. The method of claim 3, wherein the sampling comprises sampling 16 analog-to-digital conversions during a current time sampling interval.

7. The method of claim 6, wherein the discarding comprises filtering out four highest analog-to-digital conversions and four lowest analog-to-digital conversions so as to provide eight analog-to-digital conversions for determination of analyte concentration.

8. A method to determine analyte concentration in a fluid sample in contact with two electrodes, the method comprising:
   applying a voltage to the electrodes;
   sampling the magnitude of current generated in the fluid sample to provide a plurality of analog-to-digital conversions;
   discarding a subset of the plurality of analog-to-digital conversions;
   generating an analyte concentration based on remaining analog-to-digital conversion, wherein a first subset of the plurality of A/D conversions is sampled from a first pair of electrodes and a second subset of the plurality of A/D conversions is sampled from a second pair of electrodes.

9. The method of one of claims 1, 2, 3 or 8, wherein the step of discarding a subset of the plurality of A/D conversions comprises filtering out at least a highest magnitude A/D conversion and a lowest magnitude A/D conversion leaving a plurality of accepted A/D conversions.

10. The method of one of claims 1, 2, 3 or 8, wherein the step of generating an analyte concentration based on the remaining A/D conversions comprises:

calculating an average or a summation of said plurality of accepted A/D conversions; and converting said average or said summation into an analyte concentration.

11. The method according to one of claims 1, 2, 3 or 8, further comprising identifying the presence of the fluid in apposition to be detectable by the meter; and determining whether the identification is in error.

* * * * *

UNITED STATES PATENT AND TRADEMARK OFFICE
CERTIFICATE OF CORRECTION

| | |
|---|---|
| PATENT NO. | : 7,468,125 B2 |
| APPLICATION NO. | : 11/252216 |
| DATED | : December 23, 2008 |
| INVENTOR(S) | : Ulrich Kraft, Manfred Ebner and James Christol |

It is certified that error appears in the above-identified patent and that said Letters Patent is hereby corrected as shown below:

Column 14, line 22 should read -- discarding a subset of the plurality of analog-to-digital --

Signed and Sealed this

Eighth Day of June, 2010

David J. Kappos
*Director of the United States Patent and Trademark Office*